US011504703B2

(12) United States Patent
Ye et al.

(10) Patent No.: US 11,504,703 B2
(45) Date of Patent: Nov. 22, 2022

(54) METHOD FOR PARTIALLY REGENERATING METHANOL TO OLEFIN CATALYST AND METHANOL TO OLEFIN PROCESS

(71) Applicant: Dalian Institute of Chemical Physics, Chinese Academy of Sciences, Dalian (CN)

(72) Inventors: Mao Ye, Dalian (CN); Jibin Zhou, Dalian (CN); Tao Zhang, Dalian (CN); Jinling Zhang, Dalian (CN); Yinfeng Zhao, Dalian (CN); Xiangao Wang, Dalian (CN); Jinming Jia, Dalian (CN); Hailong Tang, Dalian (CN); Zhongmin Liu, Dalian (CN)

(73) Assignee: Dalian Institute of Chemical Physics, Chinese Academy of Sciences, Shahekou Dalian (CN)

( * ) Notice: Subject to any disclaimer, the term of this patent is extended or adjusted under 35 U.S.C. 154(b) by 0 days.

(21) Appl. No.: 16/767,268

(22) PCT Filed: Dec. 5, 2017

(86) PCT No.: PCT/CN2017/114567
§ 371 (c)(1),
(2) Date: May 27, 2020

(87) PCT Pub. No.: WO2019/109237
PCT Pub. Date: Jun. 13, 2019

(65) Prior Publication Data
US 2020/0324280 A1 Oct. 15, 2020

(51) Int. Cl.
*B01J 38/06* (2006.01)
*C07C 1/24* (2006.01)
(Continued)

(52) U.S. Cl.
CPC ............... *B01J 29/90* (2013.01); *B01J 29/85* (2013.01); *B01J 38/06* (2013.01); *C07C 1/24* (2013.01); *C07C 2529/85* (2013.01)

(58) Field of Classification Search
CPC ....................................................... B01J 38/06
See application file for complete search history.

(56) References Cited

U.S. PATENT DOCUMENTS

| 2002/0013505 A1* | 1/2002 | Fung ................ B01J 29/04 585/640 |
| 2007/0037692 A1* | 2/2007 | Beech ............... B01J 38/30 502/56 |
| 2010/0292071 A1* | 11/2010 | Ferrini ............ B01J 37/0045 502/55 |

FOREIGN PATENT DOCUMENTS

| AU | 20062662207 A1 | 1/2007 |
| CN | 101811072 A | 8/2010 |

(Continued)

OTHER PUBLICATIONS

Machine translation CN 104672040, accessed Mar. 11, 2022 (Year: 2022).*

(Continued)

*Primary Examiner* — Renee Robinson
*Assistant Examiner* — Alyssa L Cepluch
(74) *Attorney, Agent, or Firm* — Edwin A. Sisson, Attorney at Law, LLC; Jeffrey J. Banyas

(57) ABSTRACT

The present application discloses a method for partially regenerating a methanol to olefin catalyst, comprising: placing a deactivated methanol to olefin catalyst in a regenerator to carry out a partial regeneration reaction to obtain a regenerated catalyst; at least a portion of the regenerated catalyst has a coke amount of more than 1%. The present application discloses a methanol to olefin process, the methanol to olefin reaction is carried out in a fluidized bed (Continued)

with the use of a methanol to olefin catalyst, wherein at least a portion of the regenerated catalyst has a coke amount of more than 1%.

8 Claims, 3 Drawing Sheets

(51) Int. Cl.
*B01J 29/90* (2006.01)
*B01J 29/85* (2006.01)

(56) References Cited

FOREIGN PATENT DOCUMENTS

| | | |
|---|---|---|
| CN | 101844089 A | 9/2010 |
| CN | 101941875 A | 1/2011 |
| CN | 102276393 A | 12/2011 |
| CN | 102463138 A | 5/2012 |
| CN | 104672040 A | 6/2015 |
| JP | 2011011207 A | 1/2011 |
| KR | 20160095024 A | 8/2016 |
| RU | 2522576 C1 | 7/2014 |

OTHER PUBLICATIONS

Zuurdeeg, Boudewijn, "Extended EP—Search Report (EESR): EPO Application No. EP 17934137", dated Oct. 13, 2020.

E.V. Zelenina, "Federal Service for Intellectual Property—Search Report (FIPS) of PCT Application No. PCT/CN2017/114567", dated Feb. 9, 2021.

I.M. Kolesnikov, G.I. Vyakhirev, M.Yu. Kilyanov, V.A. Vinokurov, and S.I. KOLESNIKOV, Solid Catalysts, Their Structure, Composition And Catalytic Activity, 2000, Oil and Gas Publishing House (State Unitary Company), Moscow, Russia.

Ivan Mikhailovich Kolesnikov, Catalysis In Gas And Oil Industry, Ministry of Education and Science Manual, 2012, Gubkin Russian State University of Oil and Gas , Department of Physical and Colloidal Chemistry, Moscow.

O.V. Kemer and T.A. Antipova, Methodology For Solving Problems In The Course Of General Chemistry, Russian Federation Ministry Of Transport Methodological Manual, 2007, UHASCA.

Yu.A. Moskvichev, A.K. Grigorichev, O.S. Pavlov, Theoretical Basis Of Chemical Technology, textbook, 2nd ed. revised, 2016, 272 Pages, Lan Publishing house, Saint Petersburg, Moscow, Krasnodar, Russia.

* cited by examiner

METHOD FOR PARTIALLY REGENERATING METHANOL TO OLEFIN CATALYST AND METHANOL TO OLEFIN PROCESS

PRIORITIES AND CROSS REFERENCES

This Applications claims priority from International Application No. PCT/CN2017/114567 filed on 5 Dec. 2017, the teachings of which are incorporated by reference herein in their entirety.

TECHNICAL FIELD

The present application relates to a method for partially regenerating methanol to olefin catalyst and a regenerated catalyst, which belongs to the field of chemical catalysts.

BACKGROUND

Ethylene and propylene are important basic raw materials for the national economy and occupy an important strategic position in the development of the petrochemical and chemical industries. The raw material for producing ethylene in China is mainly naphtha, and its cost is relatively high. Industrial methanol to olefin technology starts from coal and light olefin with a high selectivity is successfully achieved by a fluidized bed process using a SAPO-based catalyst. However, the deactivation of SAPO-type catalysts will occur after reacting for a certain period of time due to coke deposition and it is necessary to carry out coke-burning for regenerating to restore the activity and selectivity of the catalyst. In the prior art, the regeneration process of the methanol to olefin catalyst uses a mixture of nitrogen and air or steam and air as the regeneration feed gas. By adjusting the amount of nitrogen or steam in the regeneration feed gas, the phenomenon of "temperature runaway" or "tail burning" in the regeneration process is avoiding. However, a large amount of greenhouse gas $CO_2$ is produced in this method, which is not conducive to environmental protection and reduces the utilization of carbon atoms in methanol.

U.S. Ser. No. 06/286,604 discloses a method for regenerating a catalyst by mixing air and steam, wherein the volume ratio of air to steam is 1:1 and the regeneration temperature is in a range of 450° C. to 480° C. In this method, the rate of coke-burning is very fast due to the presence of air. The catalytic effect of the catalyst after regeneration is comparable to that of the fresh agent, and the selectivity to the initial light olefin is not increased, and the effect thereof is equivalent to complete regeneration.

SUMMARY OF THE INVENTION

According to an aspect of the present invention, a method for partially regenerating a methanol to olefin catalyst is provided, which is capable of gasifying partial coke deposited on the deactivated catalyst with steam to partially regenerate the deactivated methanol to -olefin catalyst quickly and efficiently. It is more favorable for methanol to olefin reaction than completely regenerating the catalyst.

In the prior art, it is generally recognized by those skilled in the art that the modification and structural modification of the fresh SAPO-34 molecular sieve catalyst, such as metal heteroatom modification, ship-in-a-bottle and cage modification, etc., are performed before the MTO reaction to improve the catalytic performance of the SAPO-34 catalyst. In the method of ship-in-a-bottle and cage modification, a large molecule is formed in the molecular sieve cage based on the mechanism of the hydrocarbon pool, which not only reduces the number of acid centers in the cage, but also reduces the cage volume, thereby shortening the induction period of MTO reaction and improving the selectivity to light olefin. It is reported in the literature that the molecules that can modify the cage mainly comprise $PH_3$, $SiH_4$, $Si_2H_6$ and $B_2H_6$. However, from the perspective of partial regeneration of the deactivated catalyst, there are few literature reports and patent applications to modify the cage structure through residual coke deposition. In combination with current industrial production, it is necessary to remove coke deposition as much as possible from deactivated catalysts for complete regeneration, so as to achieve better catalyst performance. However, the inventors of the present application have found through creative research that there is a technical bias in the above recognition. The inventive discovery of the present application is that the catalytic performances of the deactivated methanol to olefin catalyst and the fully regenerated methanol to olefin catalyst are not satisfactory for the methanol to olefin reaction, but the incompletely regenerated catalyst which retains a certain amount of coke deposition has better catalytic activity and can greatly improve the selectivity to the initial light olefins and also ensure the highest selectivity of the catalyst to light olefins, thereby improving the overall selectivity to the light olefins.

The method for partially regenerating methanol to olefin catalyst, characterized in that the method comprises placing a deactivated methanol to olefin catalyst in a regenerator for a partial regeneration reaction to obtain a regenerated catalyst;

At least a portion of the regenerated catalyst has a coke amount of more than 1%. Further preferably, among the regenerated catalyst obtained by the partial regeneration reaction in the regenerator, at least a portion of the regenerated catalyst has a coke amount in a range of 1.7% to 6%.

Preferably, the lower limit of the coke amount of the regenerated catalyst obtained by the partial regeneration reaction in the regenerator is selected from 1%, 1.5%, 1.7%, 1.76%, 2%, 2.94%, 3%, 3.89% and 4%, the upper limit is selected from 2%, 2.94%, 3%, 3.89%, 4%, 4.82%, 5.16%, 5.95% and 6%.

Further preferably, the regenerated catalyst obtained by the partial regeneration reaction in the regenerator has a coke amount in a range of 2% to 6%.

In the present application, the formula for calculating the coke amount co of the catalyst is as shown in the following formula I:

$$\text{The coke amount } \omega = (m_{250°\,C.} - m_{900°\,C.})/m_{250°\,C.} \times 100\% \quad \text{Formula I}$$

In Formula I, ω is the coke amount of the catalyst in mass percentage, and $m_{250°\,C.}$ is the mass of the catalyst when the temperature is raised to 250° C., and $m_{900°\,C.}$ is the mass of the catalyst when the temperature is raised to 900° C., and the heating process is performed in air.

Preferably, in the partial regeneration reaction, steam is introduced into the regenerator.

If air or oxygen is introduced into the regenerator, the regeneration reaction is a reaction between the coke deposited on the deactivated catalyst and $O_2$. Since it is equivalent to the combustion reaction of the coke itself, it is difficult to control the degree of combustion and is difficult to obtain an incompletely regenerated catalyst; and the catalytic activity of the coke deposited on the catalyst which is not completely oxidized to $CO_2$ after reacting with $O_2$ is not high, and the selectivity to ethylene and propylene in MTO reaction is also low.

Specifically, when air is used for regenerating catalyst, even if the degree of reaction is controlled and the catalyst is not completely regenerated, partially regenerating the catalyst by coke-burning with air will cause a large change in the residual coke properties of the catalyst. The co-catalysis of the regenerated catalyst will weaken during the MTO reaction and the selectivity to light olefins cannot reach the maximum since oxygen first reacts with hydrogen to gradually convert the residual coke into heavy components, while heavy components has no catalytic activity for the methanol to olefin reaction.

As a preferred embodiment of the present application, steam is introduced into the regenerator instead of the regeneration gas containing oxygen, and the regeneration reaction in the technical solution of the present application is a reaction between the coke deposited on the deactivated catalyst and $H_2O$. During the regeneration process, the steam reacts with the coke selectively, so that the properties of the residual coke can be effectively controlled by the regeneration temperature and time, thereby the selectivity to the light olefin in the reaction may be further ensured. In the technical solution of the present application, the catalyst is in contact with steam under an inert gas atmosphere so as to avoid the influence of air on the performance of the catalyst. Further preferably, the contact time between the steam introduced into the regenerator and the deactivated methanol to olefin catalyst is in a range of 10 min to 40 min. Further preferably, the steam is introduced into the regenerator with a space velocity in a range of 4 $h^{-1}$ to 8 $h^{-1}$.

Preferably, the partial regeneration reaction is carried out at a temperature in a range of 600° C. to 750° C.;

Further preferably, the partial regeneration reaction is carried out at a temperature in a range of 710° C. to 750° C.;

Preferably, the deactivated methanol to olefin catalyst has a coke amount in a range of 7% to 12%.

Preferably, an inert gas is also introduced into the regenerator.

The inert gas is at least one selected from nitrogen, helium, argon, and helium.

Further preferably, in the partial regeneration reaction, the volume fraction of oxygen in the gas phase of the regenerator is ≤1%.

Preferably, the methanol to olefin catalyst is subjected to a methanol to olefin reaction in a fluidized bed reactor, and the deactivated methanol to olefin catalyst is transported to a regenerator for a partial regeneration reaction to obtain a regenerated catalyst, which is an incompletely regenerated catalyst. The incompletely regenerated catalyst is recycled back to the fluidized bed reactor.

In the present application, the incompletely regenerated catalyst refers to a regenerated catalyst in which the coke deposition on the catalyst is not completely removed after being regenerated, and a portion of the coke deposition remains on the catalyst. It may also be referred to as a partially regenerated catalyst.

Preferably, the catalyst is a molecular sieve catalyst.

Preferably, the methanol to olefin catalyst is a fluidized bed catalyst.

Preferably, the catalyst is a silicoaluminophosphate molecular sieve (abbreviated as SAPO molecular sieve) catalyst.

Preferably, the reactor is a fluidized bed reactor.

Preferably, an inert gas is introduced into the reactor for sweeping before the steam is introduced. Preferably, the inert gas is at least one selected from argon and nitrogen.

According to another aspect of the present invention, a methanol to olefin process is provided, wherein the methanol to olefin reaction is carried out in a fluidized bed with the use of a methanol to olefin catalyst, characterized in that at least a portion of the regenerated catalyst has a coke amount of more than 1%.

Preferably, the regenerated catalyst has a coke amount in a range of 2% to 6%.

Preferably, the regenerated catalyst is obtained by at least one of the above-described methods for partially regenerating methanol to olefin catalyst.

The beneficial effects that can be produced by this application include:

1) the catalyst is partially regenerated by gasifying coke deposited on the catalyst with steam as the regeneration gas and the gasification product are mainly CO and $H_2$, which can be recycled, and the utilization rate of carbon atoms in methanol can be improved.

2) The gasification rate of steam is slow, which is beneficial to the control of the amount of residual coke in the catalyst, the reaction of gasifying coke with steam is carried out in the vicinity of the active site of the catalyst, thereby the coke is removed selectively.

3) The MTO reaction is carried out with a catalyst partially regenerated by steam, which can greatly improve the selectivity to the initial light olefin and also ensure the highest selectivity, thereby the overall selectivity to the light olefin is improved. The selectivity to the initial light olefin of the fully regenerated catalyst is 62.57%, and the selectivity to the initial light olefin of the partially regenerated catalyst in the present process can be controlled within a range of 63% to 83%.

4) The MTO reaction is carried out with a catalyst partially regenerated by steam, the reactant of methanol is nearly completely converted, and the methanol conversion is the same as that of the fresh catalyst. The conversion of methanol with the use of the partially regenerated catalyst in the method is close to 100%.

DETAILED DESCRIPTION OF THE EMBODIMENT

The present application is described in detail below with reference to the examples, but the application is not limited to the examples.

The methanol to olefin catalyst SAPO-34 used commercially in the present application is purchased from Zhengda Energy Materials (Dalian) Co., Ltd.

The coke amount of the catalyst is measured as follows: The catalyst is heated to 250° C. in air, and the mass of the catalyst is recorded as $m_{250°\ C.}$; the catalyst is further heated to 900° C. in air, and the mass of the catalyst is recorded as $m_{900°\ C.}$; the coke amount of the catalyst is determined by the following formula I:

$$\text{The coke amount } \omega = (m_{250°\ C.} - m_{900°\ C.})/m_{250°\ C.} \times 100\% \qquad \text{Formula I}$$

Example 1

4 g of commercial methanol to olefin catalyst SAPO-34 is charged into a fixed-fluidized bed reactor to carry out a methanol to olefin reaction. The reaction raw material is a methanol aqueous solution with a concentration of 80 wt %, the reaction temperature is 490° C., the pressure is 0.1 MPa and the space velocity is 2.1 $h^{-1}$. After the catalyst is deactivated, the coke amount of the deactivated catalyst is measured to be 9.18%.

Figure 1:
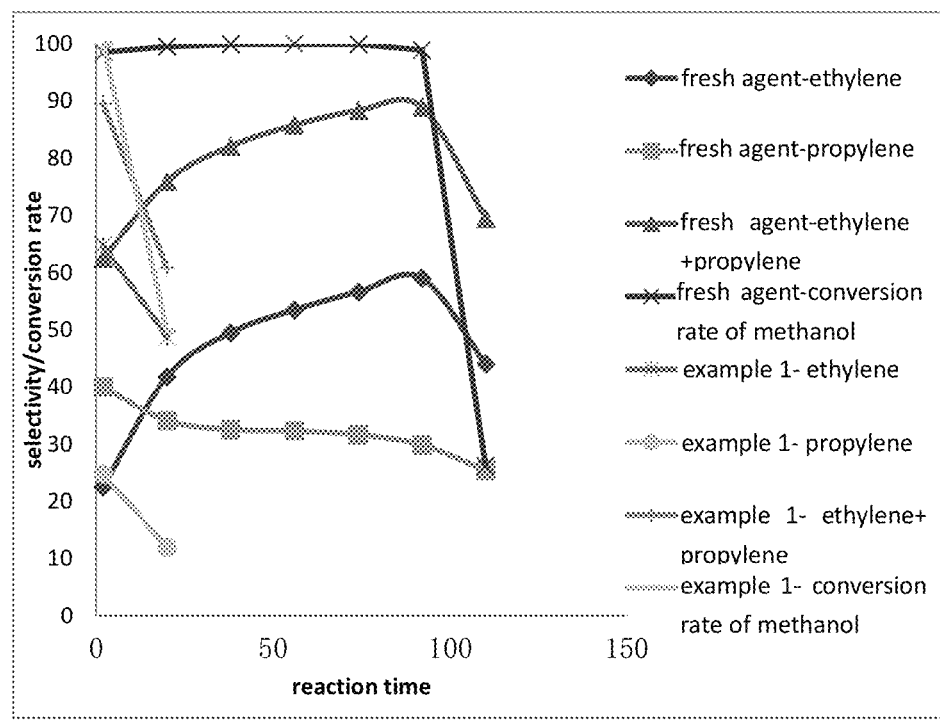
FIG. 1 is a schematic view showing the performance test results of a partially regenerated catalyst in an embodiment of the present invention.

After the catalyst is deactivated, a nitrogen gas with a flow rate of 100 mL/min is introduced into the reactor for sweeping, the temperature of the reactor heating furnace is set. When the temperature is raised to 700° C., the nitrogen gas is continuously swept for 10 minutes, and then steam is introduced with a mass space velocity of 6 $h^{-1}$, and the temperature is kept for 15 min. When the gasification of the steam is finished, a small amount of catalyst is taken to measure the coke amount. The coke amount is 5.95%. The regeneration is stopped after the temperature programming is over, the regeneration gas is switched to nitrogen gas. When the temperature of the heating furnace drops to 490° C., keep it for 20 min. A methanol aqueous solution with a concentration of 80 wt % is introduced after the temperature is stabilized, the space velocity is 2.1 $h^{-1}$, the pressure is 0.1 MPa, and an evaluation of methanol to olefin reaction is carried out. The conversion of methanol and the selectivity to olefin with the regenerated catalyst are shown in FIG. 1. In the figure, "fresh agent" means a methanol to olefin catalyst which has not been used in the examples, that is, which is used as a methanol to olefin catalyst for the first time.

Example 2

4 g of commercial methanol to olefin catalyst SAPO-34 is charged into a fixed-fluidized bed reactor to carry out a methanol to olefin reaction. The reaction raw material is a methanol aqueous solution with a concentration of 80 wt %, the reaction temperature is 490° C., the pressure is 0.1 MPa and the space velocity is 2.1 $h^{-1}$. After the catalyst is deactivated, the coke amount of the deactivated catalyst is measured to be 11.88%.

Figure 2:
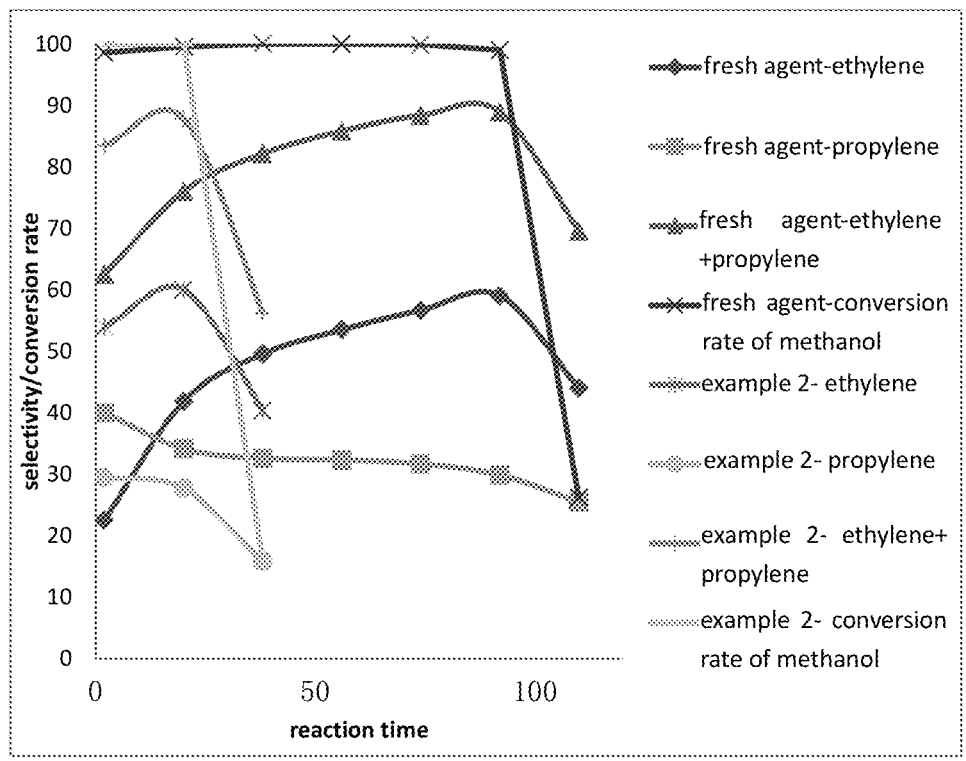
FIG. 2 is a schematic view showing the performance test results of a partially regenerated catalyst in an embodiment of the present invention.

After the catalyst is deactivated, a nitrogen gas with a flow rate of 100 mL/min is introduced into the reactor for sweeping, the temperature of the reactor heating furnace is set. When the temperature is raised to 700° C., the nitrogen gas is continuously swept for 10 minutes, and then steam is introduced with a mass space velocity of 6 $h^{-1}$, and the temperature is kept for 30 min. When the gasification of the steam is finished, a small amount of catalyst is taken to measure the coke amount. The coke amount is 4.82%. The regeneration is stopped after the temperature programming is over, the regeneration gas is switched to nitrogen gas. When the temperature of the heating furnace drops to 490° C., keep it for 20 min. A methanol aqueous solution with a concentration of 80 wt % is introduced after the temperature is stabilized, the space velocity is 2.1 $h^{-1}$, the pressure is 0.1 MPa, and an evaluation of methanol to olefin reaction is carried out. The conversion of methanol and the selectivity to olefin with the regenerated catalyst are shown in FIG. 2. In the figure, "fresh agent" means a methanol to olefin catalyst which has not been used in the examples, that is, which is used as a methanol to olefin catalyst for the first time.

Example 3

4 g of commercial methanol to olefin catalyst SAPO-34 is charged into a fixed-fluidized bed reactor to carry out a methanol to olefin reaction. The reaction raw material is a methanol aqueous solution with a concentration of 80 wt %, the reaction temperature is 490° C., the pressure is 0.1 MPa and the space velocity is 2.1 $h^{-1}$. After the catalyst is deactivated, the coke amount of the deactivated catalyst is measured to be 7.08%.

Figure 3:
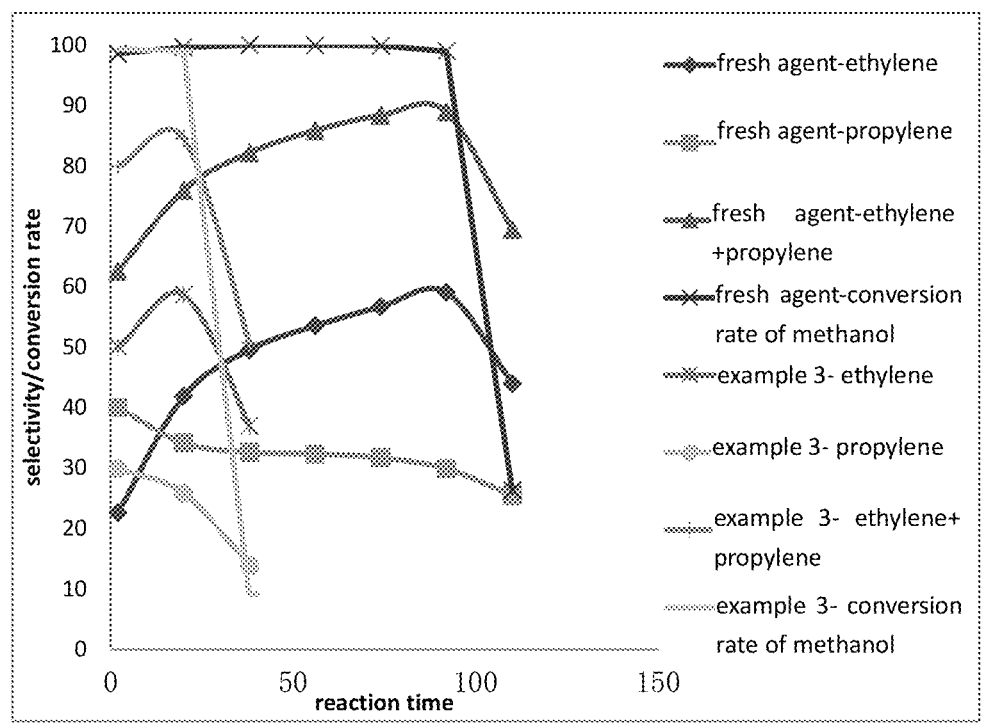
FIG. 3 is a schematic view showing the performance test results of a partially regenerated catalyst in an embodiment of the present invention.

After the catalyst is deactivated, a nitrogen gas with a flow rate of 100 mL/min is introduced into the reactor for sweeping, the temperature of the reactor heating furnace is set. When the temperature is raised to 750° C., the nitrogen is continuously swept for 10 minutes, and then steam is introduced with a mass space velocity of 6 $h^{-1}$, and the temperature is kept for 10 min. When the gasification of the steam is finished, a small amount of catalyst is taken to measure the coke amount. The coke amount is 5.16%. The regeneration is stopped after the temperature programming is over, the regeneration gas is switched to nitrogen gas. When the temperature of the heating furnace drops to 490° C., keep it for 20 min. A methanol aqueous solution with a concentration of 80 wt % is introduced after the temperature is stabilized, the space velocity is 2.1 $h^{-1}$, the pressure is 0.1 MPa, and an evaluation of methanol to olefin reaction is carried out. The conversion of methanol and the selectivity to olefin with the regenerated catalyst are shown in FIG. 3. In the figure, "fresh agent" means a methanol to olefin catalyst which has not been used in the examples, that is, which is used as a methanol to olefin catalyst for the first time.

Example 4

4 g of commercial methanol to olefin catalyst SAPO-34 is charged into a fixed-fluidized bed reactor to carry out a methanol to olefin reaction. The reaction raw material is a methanol aqueous solution with a concentration of 80 wt %, the reaction temperature is 490° C., the pressure is 0.1 MPa and the space velocity is 2.1 $h^{-1}$. After the catalyst is deactivated, the coke amount of the deactivated catalyst is measured to be 9.18%.

After the catalyst is deactivated, a nitrogen gas with a flow rate of 100 mL/min is introduced into the reactor for sweeping, the temperature of the reactor heating furnace is set. When the temperature is raised to 750° C., the nitrogen gas is continuously swept for 10 minutes, and then steam is introduced with a mass space velocity of 6 $h^{-1}$, and the temperature is kept for 20 min. When the gasification of the steam is finished, a small amount of catalyst is taken to measure the coke amount. The coke amount is 3.89%. The regeneration is stopped after the temperature programming is over, the regeneration gas is switched to nitrogen gas. When the temperature of the heating furnace drops to 490°

Figure 4:
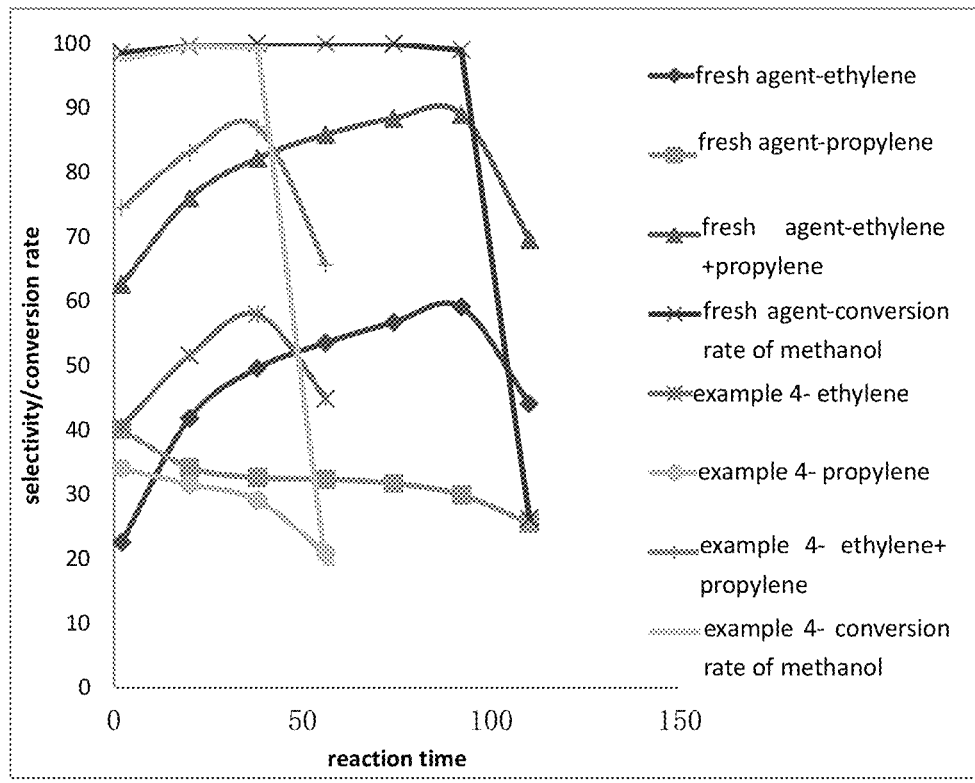
FIG. 4 is a schematic view showing the performance test results of a partially regenerated catalyst in an embodiment of the present invention.

C., keep it for 20 min. A methanol aqueous solution with a concentration of 80 wt % is introduced after the temperature is stabilized, the space velocity is 2.1 h$^{-1}$, the pressure is 0.1 MPa, and an evaluation of methanol to olefin reaction is carried out. The conversion of methanol and the selectivity to olefin with the regenerated catalyst are shown in FIG. 4. In the figure, "fresh agent" means a methanol to olefin catalyst which has not been used in the examples, that is, which is used as a methanol to olefin catalyst for the first time.

Example 5

4 g of commercial methanol to olefin catalyst SAPO-34 is charged into a fixed-fluidized bed reactor to carry out a methanol to olefin reaction. The reaction raw material is a methanol aqueous solution with a concentration of 80 wt %, the reaction temperature is 490° C., the pressure is 0.1 MPa and the space velocity is 2.1 h$^{-1}$. After the catalyst is deactivated, the coke amount of the deactivated catalyst is measured to be 9.18%.

Figure 5:
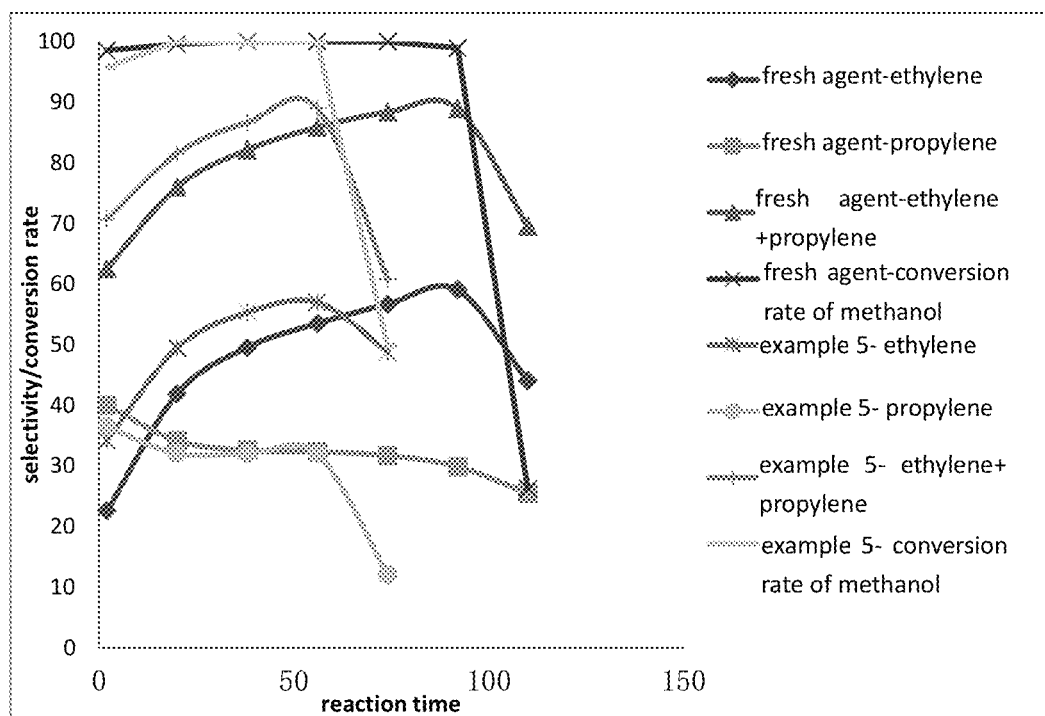
FIG. 5 is a schematic view showing the performance test results of a partially regenerated catalyst in an embodiment of the present invention.

After the catalyst is deactivated, a nitrogen gas with a flow rate of 100 mL/min is introduced into the reactor for sweeping, the temperature of the reactor heating furnace is set. When the temperature is raised to 750° C., the nitrogen gas is continuously swept for 10 minutes, and then steam is introduced with a mass space velocity of 6 h$^{-1}$, and the temperature is kept for 30 min. When the gasification of the steam is finished, a small amount of catalyst is taken to measure the coke amount. The coke amount is 2.94%. The regeneration is stopped after the temperature programming is over, the regeneration gas is switched to nitrogen gas. When the temperature of the heating furnace drops to 490° C., keep it for 20 min. A methanol aqueous solution with a concentration of 80 wt % is introduced after the temperature is stabilized, the space velocity is 2.1 h$^{-1}$, the pressure is 0.1 MPa, and an evaluation of methanol to olefin reaction is carried out. The conversion of methanol and the selectivity to olefin with the regenerated catalyst are shown in FIG. 5. In the figure, "fresh agent" means a methanol to olefin catalyst which has not been used in the examples, that is, which is used as a methanol to olefin catalyst for the first time.

Example 6

4 g of commercial methanol to olefin catalyst SAPO-34 is charged into a fixed-fluidized bed reactor to carry out a methanol to olefin reaction. The reaction raw material is a methanol aqueous solution with a concentration of 80 wt %, the reaction temperature is 490° C., the pressure is 0.1 MPa and the space velocity is 2.1 h$^{-1}$. After the catalyst is deactivated, the coke amount of the deactivated catalyst is measured to be 9.18%.

Figure 6:
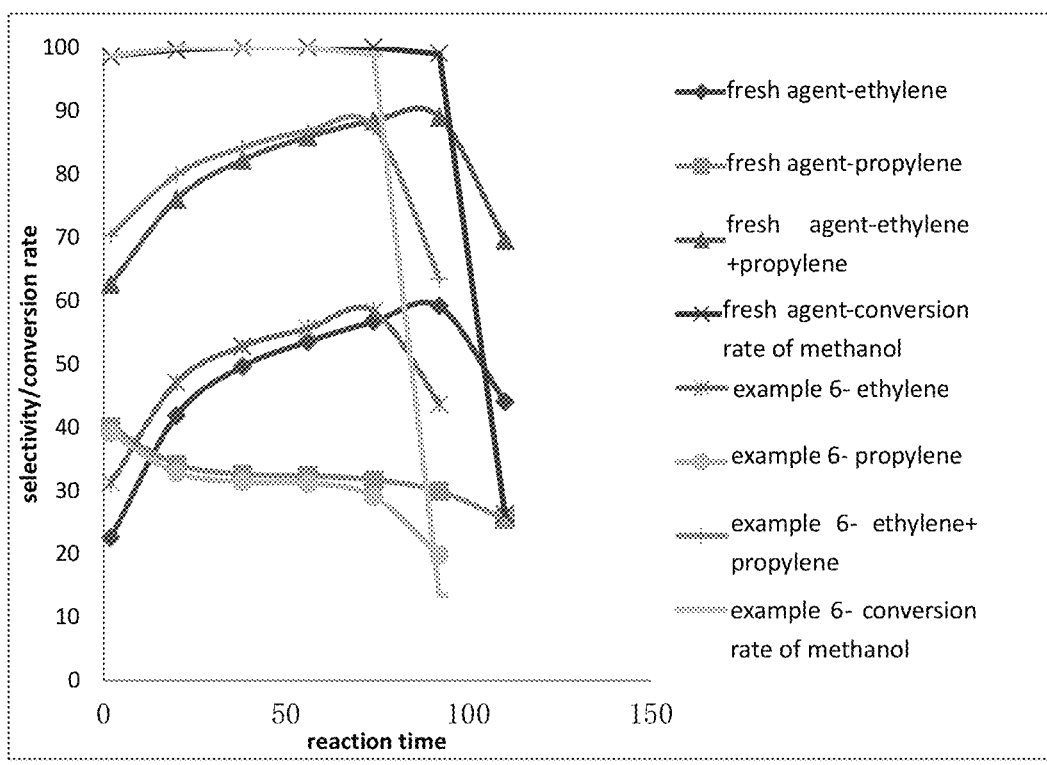
FIG. 6 is a schematic view showing the performance test results of a partially regenerated catalyst in an embodiment of the present invention.

After the catalyst is deactivated, a nitrogen gas with a flow rate of 100 mL/min is introduced into the reactor for sweeping, the temperature of the reactor heating furnace is set. When the temperature is raised to 750° C., the nitrogen gas is continuously swept for 10 minutes, and then steam is introduced with a mass space velocity of 6 h$^{-1}$, and the temperature is kept for 40 min. When the gasification of the steam is finished, a small amount of catalyst is taken to measure the coke amount. The coke amount is 1.76%. The regeneration is stopped after the temperature programming is over, the regeneration gas is switched to nitrogen gas. When the temperature of the heating furnace drops to 490° C., keep it for 20 min. A methanol aqueous solution with a concentration of 80 wt % is introduced after the temperature is stabilized, the space velocity is 2.1 h$^{-1}$, the pressure is 0.1 MPa, and an evaluation of methanol to olefin reaction is carried out. The conversion of methanol and the selectivity to olefin with the regenerated catalyst are shown in FIG. 6. In the figure, "fresh agent" means a methanol to olefin catalyst which has not been used in the examples, that is, which is used as a methanol to olefin catalyst for the first time.

The above are only a few examples of the present application, and are not intended to limit the present application in any way. Although the present application is disclosed in the above with preferred example, it is not intended to limit the present application. Any one skilled in the art can understand that other changes and modifications by using the above technical content without departing from the scope of the technical solution of the present application are equivalent to equivalent embodiments and belong to the scope of the technical solution.

The invention claimed is:

1. A methanol to olefin process comprising:
   placing a deactivated methanol to olefin catalyst in a regenerator;
   partially regenerating the deactivated methanol to olefin catalyst by gasifying coke deposited on the deactivated methanol to olefin catalyst with regeneration gas which consists of steam, to obtain a regenerated catalyst, wherein at least a portion of the regenerated catalyst has a coke amount in a range from 3.89 wt % to 6 wt % and wherein the regeneration gas does not include oxygen; and
   carrying out a methanol to olefin reaction in a fluidized bed reactor comprising the regenerated catalyst.

2. The methanol to olefin process according to claim 1, wherein the partial regeneration reaction is carried out at a temperature in a range of 710° C. to 750° C.

3. The methanol to olefin process according to claim 1, wherein a contact time between the steam and the deactivated methanol to olefin catalyst is in a range of 10 min to 40 min.

4. The methanol to olefin process according to claim 3, wherein the steam is introduced into the regenerator with a space velocity in a range of 4 h$^{-1}$ to 8 h$^{-1}$.

5. The methanol to olefin process according to claim 1, wherein the partial regeneration reaction is carried out at a temperature in a range of 600° C. to 750° C.

6. The methanol to olefin process according to claim 1, wherein the deactivated methanol to olefin catalyst has a coke amount in a range of 7 wt % to 12 wt %.

7. The methanol to olefin process according to claim 1, wherein an inert gas is also introduced into the regenerator and the inert gas is at least one selected from nitrogen, helium, argon, and neon.

8. The methanol to olefin process according to claim 1 further comprising:
   carrying out a methanol to olefin reaction in a fluidized bed reactor comprising a methanol to olefin catalyst which contains a silicoaluminophosphate molecular sieve, wherein the reaction produces the deactivated methanol to olefin catalyst, and
   recycling the regenerated catalyst to the fluidized bed reactor.

* * * * *